United States Patent
Pratt

[11] Patent Number: 6,058,790
[45] Date of Patent: May 9, 2000

[54] ADJUSTABLE LENGTH SAMPLER TUBE

[76] Inventor: David W. Pratt, 5419 Dahlgren, New Port Richey, Fla. 34652

[21] Appl. No.: 09/237,478

[22] Filed: Jan. 26, 1999

[51] Int. Cl.$^7$ .................................................. G01N 1/12
[52] U.S. Cl. .................................... 73/864.62; 73/864.73
[58] Field of Search ........................... 73/864.62, 864.73, 73/864.52, 864.63, 863.84, 864.02, 152.23; 166/162–169

[56] References Cited

U.S. PATENT DOCUMENTS

| | | | |
|---|---|---|---|
| 164,451 | 6/1875 | Hellen ................................. | 73/864.73 |
| 293,423 | 2/1884 | Contant ............................... | 73/864.73 |
| 4,338,826 | 7/1982 | Jacoby et al. ....................... | 73/864.62 |
| 4,610,171 | 9/1986 | Nason ................................. | 73/864.62 |
| 5,507,194 | 4/1996 | Scavuzzo et al. .................. | 73/864.63 |
| 5,597,966 | 1/1997 | Timmons ............................ | 73/864.63 |
| 5,902,940 | 9/1997 | Stern ................................... | 73/864.63 |

*Primary Examiner*—Hezron Williams
*Assistant Examiner*—Chad Soliz
*Attorney, Agent, or Firm*—Smith & Hopen, P.A.; Ronald E. Smith

[57] ABSTRACT

A liquid sampler tube of elongate, cylindrical construction has an accordion fold formed along a predetermined extent of its main body so that the liquid sampler tube can be shortened when in storage or in transport and returned to its initial length when ready for use. In a second embodiment, a telescoping construction supplants the accordion fold. In a third embodiment, the elongate main body is formed of a flexible, flat hose material so that it can be rolled into a rolled configuration for storage or transport and unrolled when ready for use. The shortening of the liquid sampler tube enables a greater number of liquid sampler tubes to occupy a given space relative to the number of liquid sampler tubes of standard, unshortened length.

1 Claim, 3 Drawing Sheets

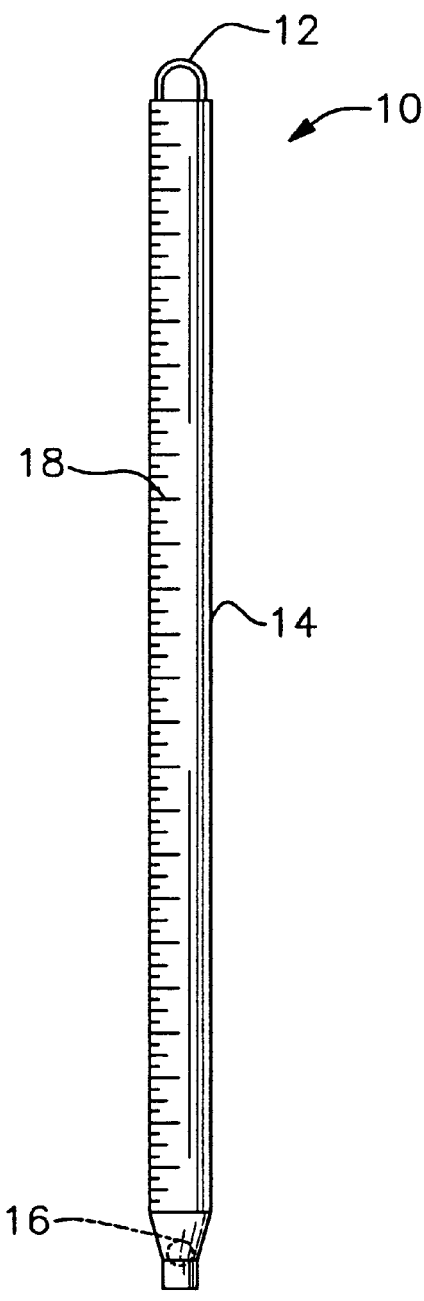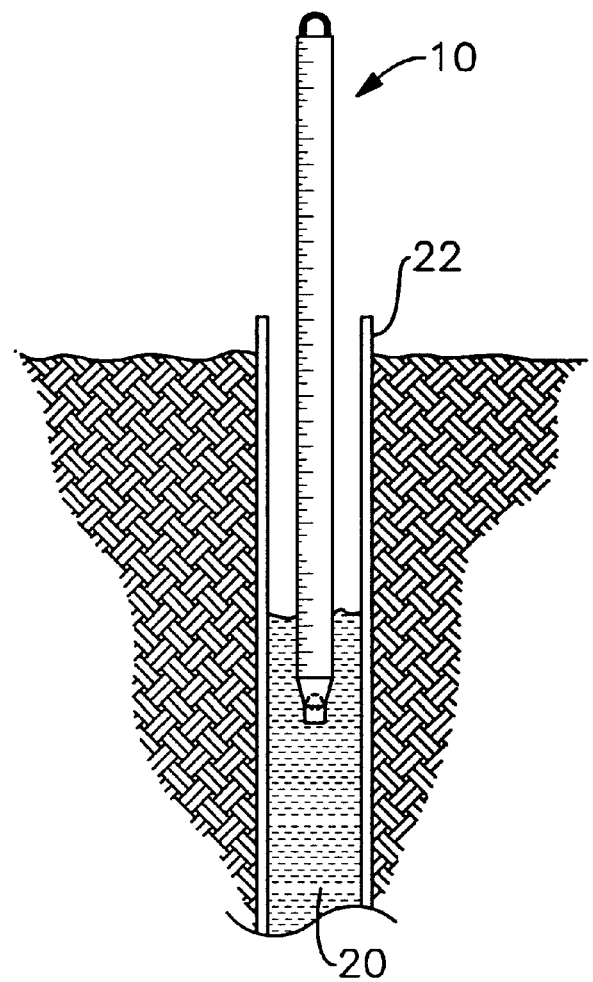
Fig. 1
Prior Art
Fig. 2
Prior Art

ADJUSTABLE LENGTH SAMPLER TUBE

BACKGROUND OF THE INVENTION

1. Field of the Invention

This invention relates, generally, to tools used to collect liquid samples for testing purposes. More particularly, it relates to a liquid sampler tube having an adjustable length so that it can be shortened to save space when in storage or in transport.

2. Description of the Prior Art

Liquid sampler tubes are elongate, cylindrical tubes that are lowered into wells or other liquid reservoirs to collect liquid samples therefrom. A check valve in the lowermost end of the tube opens automatically to allow liquid to flow into the hollow interior of the tube as it is being lowered into liquid held in a well or other reservoir. The check valve closes when the tube is lifted or displaced upwardly as it is removed from the body of liquid, thereby trapping a predetermined amount of liquid within said hollow interior. The liquid is then subjected to chemical analysis or other tests for a wide variety of purposes.

Liquid sampler tubes are typically made of plastic and are mass produceable so they are relatively inexpensive to manufacture. However, due to their elongate, cylindrical shape, they are not particularly inexpensive to store and to transport.

What is needed, then, is a way to reduce the storage and transportation costs associated with liquid sampler tubes.

However, it was not obvious to those of ordinary skill in this art how the needed improvements could be provided, in view of the art considered as a whole at the time the present invention was made.

SUMMARY OF THE INVENTION

The long-standing but heretofore unfulfilled need for an innovation that overcomes the limitations of the prior art is now met by a new, useful, and nonobvious invention. The present invention is a liquid sampler tube that includes an elongate, hollow tube having a handle means at a first end thereof, a check valve means at a second end thereof, and an elongate main body therebetween of predetermined initial length. A shortening means is provided for selectively reducing the predetermined initial length to a shortened length for storage or transportation purposes and for selectively increasing the shortened length to restore it to the initial predetermined length for use. Accordingly, a predetermined amount of space holds an increased number of shortened liquid sampler tubes relative to the amount of space required to hold an equal number of liquid sampler tubes having said unshortened predetermined initial length.

In a first embodiment, the shortening means is an accordion-fold formed in the elongate main body of the liquid sampler tube along its extent.

In a second embodiment, the shortening means is a telescoping means.

In a third embodiment, the shortening means is provided by forming the elongate main body of a flexible, flat hose material and rolling said flexible, flat hose material into a rolled configuration.

It is a primary object of this invention to provide an adjustable length liquid sampler tube that, when its length has been shortened, occupies less space than the liquid sampler tubes heretofore known, thereby reducing storage and transportation costs.

Another object is to provide a liquid sampler tube that is easily foreshortened in length and that is just as easily restored to its initial length.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a side elevational view of a liquid sampler tube of the prior art;

FIG. 2 is a side elevational, partially sectional view depicting use of a liquid sampler tube in sampling well water;

DETAILED DESCRIPTION OF THE PREFERRED EMBODIMENT

Figure 3:
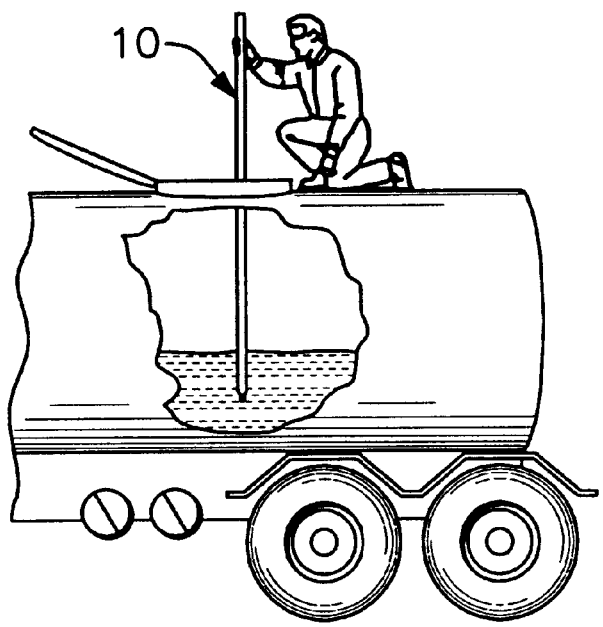
FIG. 3 is a side elevational view depicting use of a liquid sampler tube to sample liquid carried in a tanker truck.

Referring now to FIG. 1, it will there be seen that an industry standard liquid sampler tube is denoted as a whole by the reference numeral 10. Liquid sampler tube 10 includes a handle means 12 in the form of a loop at its upper or proximal end, an elongate hollow main body 14 of cylindrical construction for receiving liquid, and a check valve means including a free floating ball 16 in its lower or distal free end. Ball 16 floats freely to allow liquid to enter into main body 14 at said lowermost end when liquid sampler tube 10 is being lowered into a body of liquid, but said ball 16 seats against a valve seat and prevents liquid from flowing out of main body 14 when said main body is lifted from said body of liquid. Graduation marks 18 enable the user to measure the amount of liquid collected within main body 14.

A rope or other suitable connection means, not shown, is secured to handle means 12 if liquid sampler tube 10 is to be lowered to a depth that exceeds the length of main body 14.

One common use of liquid sampler 10 is to sample water 20 (or other liquid) in a well 22 as depicted in FIG. 2.

Another common use is to retrieve a sample of gasoline, kerosene, or the like from the hold of a tanker truck as depicted in FIG. 3. Note that the fixed length of industry standard liquid sampler tube 10 may be manufactured to any manageable length as desired. Liquid sampler tube 10 can also be used to sample liquid held in the hold of a ship, not shown, and in many other unillustrated applications.

Figure 4:
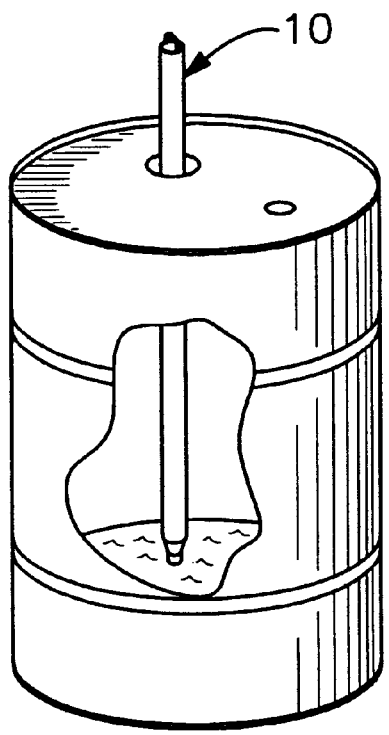
FIG. 4 is a perspective view depicting use of a liquid sampler tube to sample liquid contained in a fifty gallon drum.

FIG. 4 depicts a conventional liquid sampler 10 in use to sample liquid contained within a drum, such as a fifty gallon drum, or the like.

Figure 5:
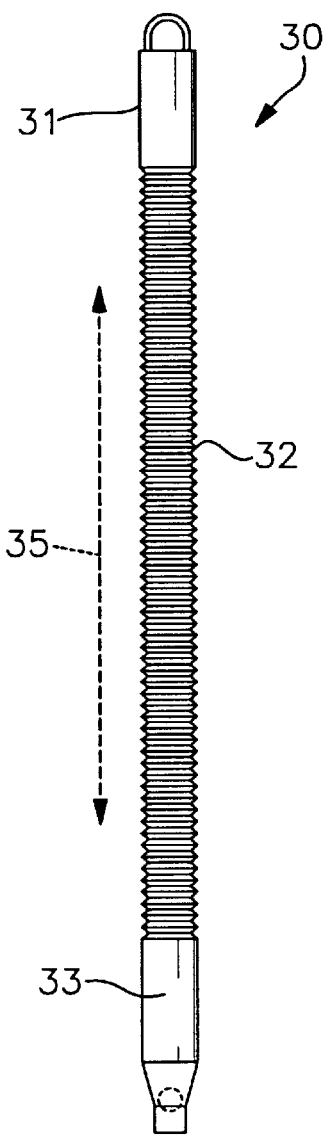
FIG. 5 is a side elevational view depicting a first embodiment of the novel adjustable length liquid sampler tube.

The preferred embodiment of the invention is depicted in FIG. 5 and is denoted 30 as a whole. A major percentage of main body 32 has an accordion-like construction as depicted so that it can be foreshortened when said accordion-like section is compressed, i.e., when the opposite ends of liquid sampler tube 10 are manually displaced toward one another. This enables it to be reduced in length to less than fifty percent (50%) of its initial length so that at least twice as many liquid sampler tubes may be stored and shipped in the same space as the liquid sampler tubes of the prior art.

The accordion-like construction also facilitates returning the liquid sampler to its initial, unshortened length so that it can be used in the conventional way in wells, holds, drums, and the like.

Note that about four inches or so of elongate main body 32 at each end thereof is not provided with the annular folds that collectively provide the accordion-effect. Said unaltered spaces are denoted 31 and 33 respectively. Tubular spaces 31, 33 provide gripping surfaces where a user may grasp liquid sampler 10 at its opposite ends by the hands to shorten it or to lengthen it, as suggested by double-headed arrow 35 in FIG. 5.

Figure 6:
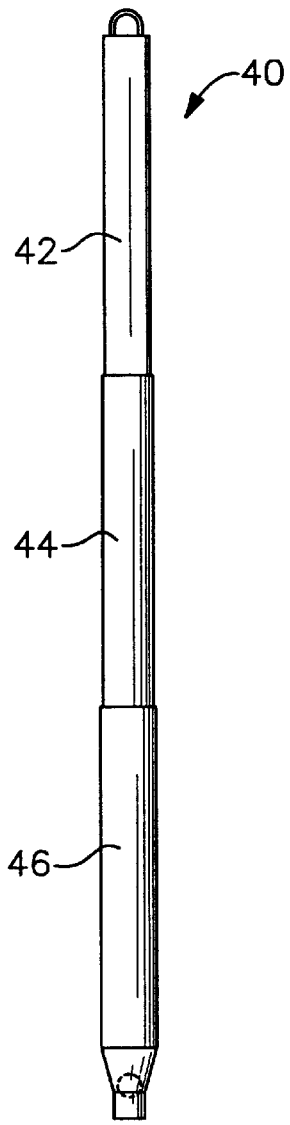
FIG. 6 is a side elevational view depicting a second embodiment of the novel adjustable length liquid sampler tube.

Another feasible way to shorten liquid sampler tube 10 for storage or shipping purposes is denoted 40 as a whole in FIG. 6. In this telescoping design, upper section 42 is slideingly received into middle section 44 and said middle section 44 is slideingly received into lower section 46. This reduces the overall length of liquid sampler tube 40 to about one-third its initial length for storage and shipping purposes. Like the preferred embodiment, it is a simple matter to restore liquid sampler tube 40 to its initial length to prepare it for use.

Figure 7:
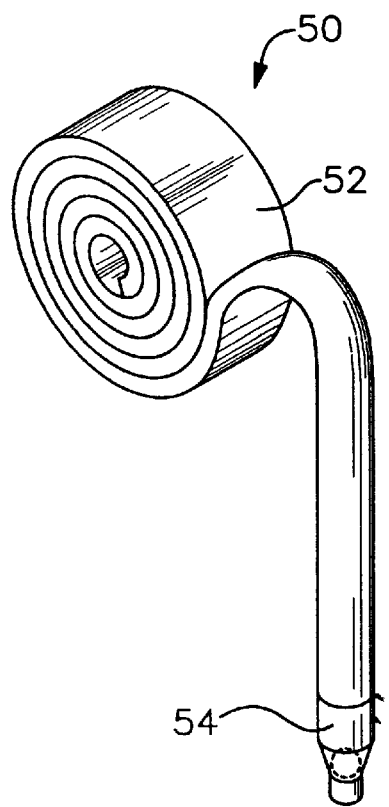
FIG. 7 is a perspective view depicting a third embodiment of the novel adjustable length liquid sampler tube.

A third embodiment, denoted 50 as a whole, is depicted in FIG. 7. In this embodiment, main body 52 is formed of a flat, flexible hose material that can be rolled into a rolled configuration as depicted. This also greatly reduces the amount of space occupied by liquid sampler tube 50 when it is in storage or in transport. Liquid flowing past ball valve 16 restores main body 52 to its initial configuration when liquid sampler tube 50 is unrolled and in use.

A weight means 54 of predetermined mass may be added to elongate main body 52 near its lowermost end to ensure straightening of the flexible hose material as it is lowered into a body of water.

This invention represents a major breakthrough in the art of liquid sampler tubes. Being drawn to a pioneering invention, the claims that follow are entitled, as a matter of law, to broad interpretation to protect the heart or essence of the invention from piracy.

It will thus be seen that the objects set forth above, and those made apparent from the foregoing description, are efficiently attained. Since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A liquid sampler tube, comprising:

an elongate, hollow tube having a handle means at a first end thereof, a check valve means at a second end thereof, and an elongate main body therebetween having a predetermined length;

shortening means for selectively reducing said predetermined length to a shortened length and for selectively increasing said shortened length to said predetermined length, wherein said shortening means is an accordion-fold formed along the extent of said elongate main body;

whereby a predetermined amount of space holds an increased number of shortened liquid sampler tubes relative to an equal number of liquid sampler tubes having said predetermined length; and whereby a liquid sampler tube of shortened length is restored to its predetermined length prior to use.

* * * * *